US009909688B2

(12) United States Patent
Gaines et al.

(10) Patent No.: US 9,909,688 B2
(45) Date of Patent: Mar. 6, 2018

(54) ENTERAL FEEDING PUMP CERTIFICATION

(71) Applicant: Covidien LP, Mansfield, MA (US)

(72) Inventors: Robert Gaines, Lake Saint Louis, MO (US); Christopher Knauper, St. Charles, MO (US); John Holste, Hamburg, IL (US)

(73) Assignee: KPR U.S., LLC, Mansfield, MA (US)

( * ) Notice: Subject to any disclaimer, the term of this patent is extended or adjusted under 35 U.S.C. 154(b) by 0 days.

(21) Appl. No.: 14/729,748

(22) Filed: Jun. 3, 2015

(65) Prior Publication Data
US 2015/0342835 A1 Dec. 3, 2015

Related U.S. Application Data

(60) Provisional application No. 62/007,102, filed on Jun. 3, 2014.

(51) Int. Cl.
| | |
|---|---|
| *A61J 15/00* | (2006.01) |
| *G06F 19/00* | (2011.01) |
| *F16K 37/00* | (2006.01) |
| *F15B 19/00* | (2006.01) |
| *A61M 5/14* | (2006.01) |

(52) U.S. Cl.
CPC ....... *F16K 37/0075* (2013.01); *A61J 15/0076* (2015.05); *F15B 19/005* (2013.01); *G06F 19/3412* (2013.01); *G06F 19/3468* (2013.01); *A61M 5/14* (2013.01); *A61M 2202/0482* (2013.01); *A61M 2205/3375* (2013.01); *A61M 2205/3576* (2013.01); *A61M 2205/50* (2013.01); *A61M 2205/52* (2013.01); *G06F 19/3475* (2013.01)

(58) Field of Classification Search
CPC ............ G06Q 30/018; G06F 19/3418; G06F 19/3456; G06F 19/3462; G06F 19/3406; G06F 19/3412; H04L 2209/88; A61B 5/0002; A61B 8/4427; A61B 5/11; A61B 5/0022; A61J 15/0076; A61J 15/0088; A61J 7/0418; A61M 5/142; A61M 2205/52

See application file for complete search history.

(56) References Cited

U.S. PATENT DOCUMENTS

| 7,794,423 B2 | 9/2010 | Gaines et al. |
| 2001/0031944 A1 | 10/2001 | Peterson et al. |

(Continued)

FOREIGN PATENT DOCUMENTS

WO 2014043499 A1 3/2014

OTHER PUBLICATIONS

International Search Report dated Sep. 4, 2015 in related application PCT/US2015/033963, 4 pages.

(Continued)

*Primary Examiner* — Manuel L Barbee
(74) *Attorney, Agent, or Firm* — Adnan H. Bohri

(57) ABSTRACT

A method of performing a certification on an enteral feeding pump based on at least one operating parameter of the pump includes communicating certification information between the pump and a certification application remote from the pump. The at least one operating parameter is compared to a specified operating metric to verify that the at least one operating parameter of the pump is within the specified operating metric.

18 Claims, 13 Drawing Sheets

(56) References Cited

U.S. PATENT DOCUMENTS

| | | | | |
|---|---|---|---|---|
| 2002/0016568 A1* | 2/2002 | Lebel | ............... | A61M 5/14276 |
| | | | | 604/131 |
| 2005/0278054 A1* | 12/2005 | Gaines | .............. | A61M 5/16804 |
| | | | | 700/110 |
| 2013/0253420 A1* | 9/2013 | Favreau | .................. | F04B 49/10 |
| | | | | 604/67 |
| 2014/0031784 A1* | 1/2014 | Flynn | ................. | G06F 19/3468 |
| | | | | 604/500 |

OTHER PUBLICATIONS

Written Opinion of the International Searching Authority dated Sep. 4, 2015 in related application PCT/US2015/033963, 8 pages.
Office action dated Oct. 5, 2017 in related U.S. Appl. No. 14/729,748, 23 pages.

* cited by examiner

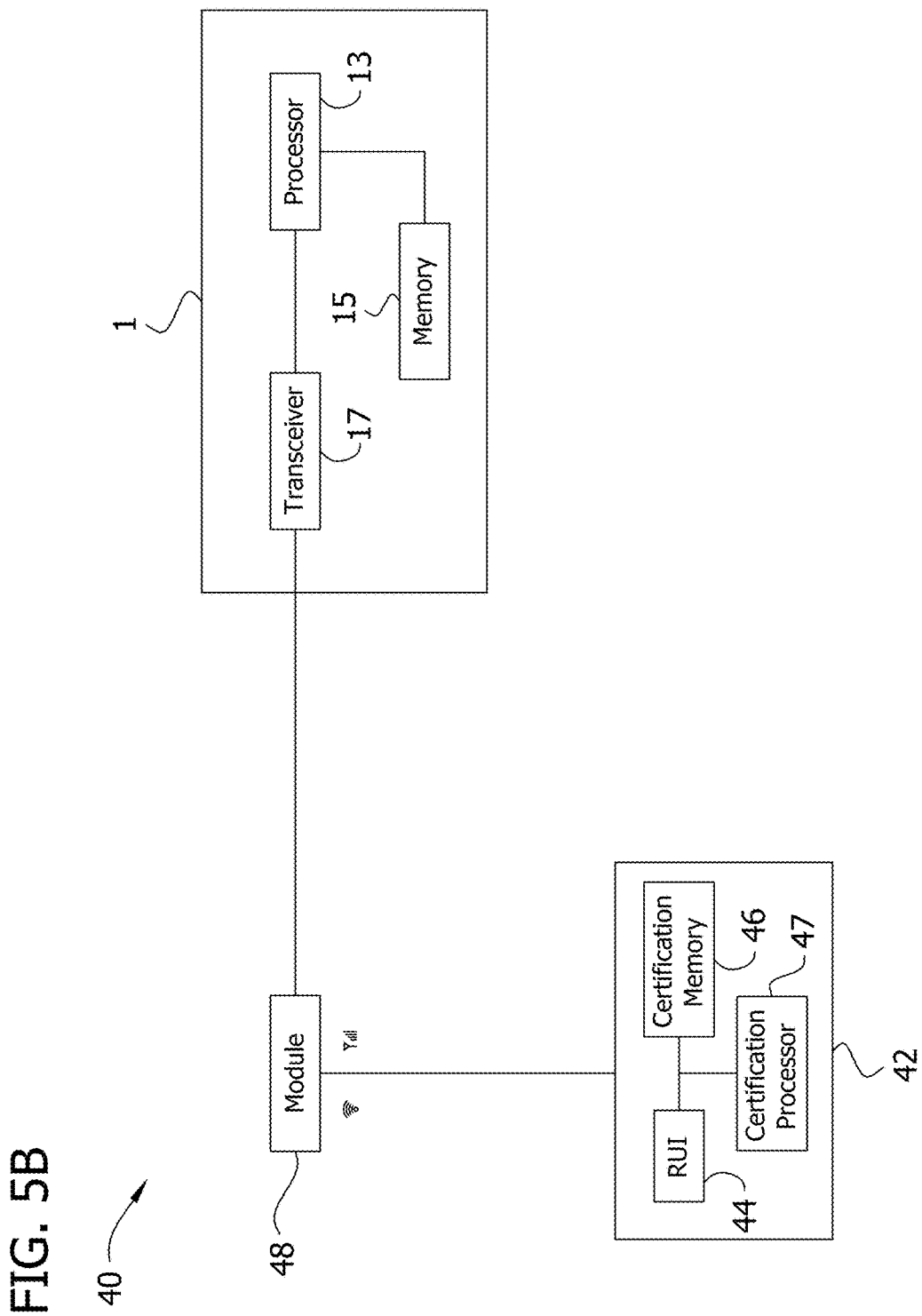

ENTERAL FEEDING PUMP CERTIFICATION

CROSS-REFERENCE TO RELATED APPLICATION

This application claims the benefit under 35 U.S.C. § 119 to U.S. Patent Application No. 62/007,102, filed on Jun. 3, 2014, the complete disclosure of which is incorporated herein by reference for all purposes.

BACKGROUND

The present invention generally relates to a certification system for a pump, and more particularly, to a wireless certification system for verifying that certain components of a pump are functioning properly, within a predetermined operational range.

Pumps are frequently used to deliver nutritional and medicinal fluids to patients. It may be important to ensure consistent and accurate delivery of these fluids for the health and safety of the patient. Accordingly, pumps may be certified on an occasional or more frequent schedule. During certification, components of the pump are tested to verify that they are functioning properly, within a predetermined operational range. Prior art certification systems may require an operator to use a special feeding set, which requires the operator to retrieve the pump from the field and perform a manual certification. This method of certification is costly and interrupts patient use of the pump.

SUMMARY

In one aspect, a method of performing a certification on an enteral feeding pump based on at least one operating parameter of the pump generally comprises communicating certification information between the pump and a certification application remote from the pump. The at least one operating parameter is compared to a specified operating metric to verify that the at least one operating parameter of the pump is within the specified operating metric.

In some embodiments, plural distinct operating parameters of the pump are determined.

In certain embodiment, the at least one operating parameter of the pump is determined during delivery of nutritional liquid to the patient In some embodiments, the certification information is wirelessly communicated between the pump and the certification application.

In certain embodiments, the at least one operating parameter is transmitted to the remote certification application.

In some embodiments, the processor in the pump receives the specified operating metric from the remote certification application and compares the at least one operating parameter against the specified operating metric.

In certain embodiments, the processor makes a certification determination whether the at least one operating parameter is within the received specified operating metric and stores the certification determination in a memory of the pump.

In some embodiments, the certification determination is transmitted from the pump to the remote certification application.

In certain embodiments, a manual certification is initiated to determine the at least one operating parameter. The manual certification comprises at least one certification step performed manually by a person. The at least one operating parameter is transmitted to the certification application.

In some embodiments, the certification application identifies the specified operating metric.

In another aspect, an enteral feeding pump certification system generally comprises an enteral feeding pump for use with a nutritional liquid feeding set to deliver nutritional liquid through the feeding set. The enteral feeding pump includes a processor configured to determine at least one operating parameter of the enteral feeding pump and a transceiver. A certification application is remote from the enteral feeding pump and includes instructions stored on computer readable medium and a certification application processor configured to execute the instructions. The certification application is configured for communication with the transceiver of the enteral feeding pump for performing a certification operation of the enteral feeding pump. One of the pump processor and the certification application processor is configured to compare the at least one operating parameter of the enteral feeding pump to a specified operating metric. One of the pump processor and the certification application processor is further configured to provide verification that the at least one operating parameter of the enteral feeding pump is within the specified operating metric.

In certain embodiments, a user interface displays information relating to the certification application and allows user interaction with the certification application.

In some embodiments, a memory stores information relating to the certification application.

In certain embodiments, the certification application identifies the specified operating metric.

In a another aspect, an enteral feeding pump for use with a nutritional liquid feeding set to deliver nutritional liquid through the feeding set generally comprises a housing capable of receiving at least a portion of the feeding set. A pumping device is supported by the housing and configured to act on the feeding set to produce fluid flow in the feeding set when the feeding set is received by the housing. A processor is configured to determine at least one operating parameter of the enteral feeding pump. A memory stores the at least one operating parameter. A transceiver is configured for communication of certification information with a certification application remote from the enteral feeding pump.

In some embodiments, the processor is configured to determine plural distinct operating parameters and the memory is configured to store said plural distinct operating parameters.

In certain embodiments, the processor is configured to determine the at least one operating parameter and the memory is configured to store the at least one operating parameter during operation of the enteral feeding pump to supply the nutritional liquid to a patient.

In some embodiments, the transceiver is configured for wireless communication with the remote certification application.

In certain embodiments, the transceiver is configured to transmit the at least one operating parameter to the remote certification application for evaluation against a specified operating metric.

In some embodiments, the transceiver is configured to receive a signal including the specified operating metric from the remote certification application and the processor is configured to evaluate the at least one operating parameter against the received specified operating metric.

In certain embodiments, the processor is configured to make a certification determination whether the at least one operating parameter is within the received operating metric and to store the certification determination in the memory.

In some embodiments, the transceiver is configured to transmit the certification determination to the remote certification application.

In certain embodiments, the processor is configured to send a signal recommending a full certification procedure be performed on the pump if the processor evaluates the at least one operating parameter to be outside of the specified operating metric.

In some embodiments, the transceiver is configured to transmit the at least one operating parameter to the remote certification application for evaluation by the remote certification application against a specified operating metric identified by the remote certification application.

Other objects and features will be in part apparent and in part pointed out hereinafter.

BRIEF DESCRIPTION OF THE DRAWINGS

FIG. 5B is a block diagram schematically illustrating another embodiment of a certification system;

Corresponding reference characters indicate corresponding parts throughout the drawings.

DETAILED DESCRIPTION

Figure 1:
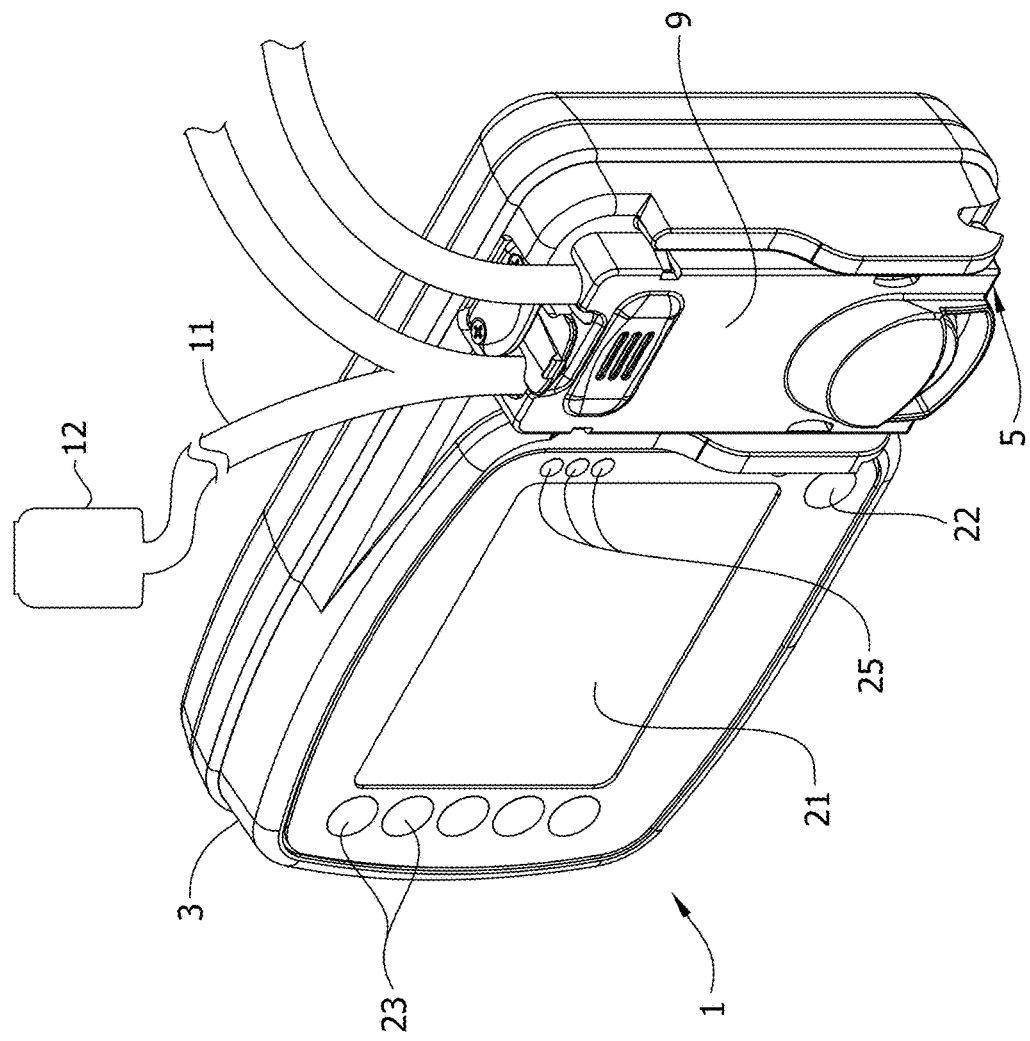
FIG. 1 is a perspective of an enteral feeding pump and a fragmentary portion of a feeding set received on the pump.

There is disclosed a method of performing a certification on an enteral feeding pump based on at least one operating parameter of the pump, the method comprising communicating certification information between the pump and a certification application remote from the pump; and verifying that the at least one operating parameter is within a specified operating metric. Communicating certification information can comprise wirelessly communicating the certification information. In some cases, communicating the certification information comprises receiving the at least one operating parameter at the certification application, and wherein verifying that the at least one operating parameter is within a specified operating metric comprises comparing the received at least one operating parameter to the specified operating metric. Verifying that the at least one operating parameter is within a specified operating metric can comprise comparing using a processor in the pump, the at least one operating parameter to the specified operating metric, and wherein communicating the certification information comprises transmitting a verification that the compared at least one operating parameter is within the specified operating metric. In some cases, communicating certification information comprises transmitting the at least one operating parameter to the certification application. The method can further comprise receiving the transmitted at least one operating parameter at the certification application remote from the pump. In some cases, verifying that the at least one operating parameter is within a specified operating metric comprises comparing using a processor at the certification application the received at least one operating parameter to the specified operating metric. Communicating certification information can comprise receiving at the pump the specified operating metric from the certification application, and wherein verifying using a processor in the pump the at least one operating parameter against the specified operating metric. The method can further comprise delivering nutritional liquid to a patient, wherein determining the at least one operating parameter of the pump is performed during delivery of the nutritional liquid to the patient. The method can further comprise making a certification determination whether the at least one operating parameter is within the received specified operating metric and storing the certification determination in a memory of the pump. The method can further comprise transmitting the certification determination from the pump to the remote certification application. In some cases, verifying that the at least one operating parameter is within a specified operating metric comprises receiving a manual certification instruction to determine the at least one operating parameter, the manual certification instruction comprising at least one certification step performed manually by a person. The specified operating metric can be identified by the certification application. The at least one operating parameter can include a first operating parameter with a first specified operating metric and a second operating parameter selected from the group consisting of a status of an ultrasonic sensor in the pump, a status of a power button in the pump, a status or position of a rotor encoder in the pump, and a status of an accelerometer in the pump, motor current, and ultrasonic sensor voltage with a corresponding second specified operating metric, and wherein verifying that the at least one operating parameter comprises verifying using a processor at the certification application that the first operating parameter is within the first operating metric, and verifying using a processor in the pump that the second operating parameter is within the second operating metric.

There is also disclosed an enteral feeding pump certification system comprising an enteral feeding pump for use with a nutritional liquid feeding set to deliver nutritional liquid through the feeding set, the enteral feeding pump including a processor configured to determine at least one operating parameter of the enteral feeding pump and a transceiver in operative communication with the processor; and a certification application remote from the enteral feeding pump and configured for communication with the transceiver, the certification application including a certification application processor configured to execute a certification operation. One of the pump processor and the certification application processor is typically configured to compare the at least one operating parameter to a specified operating metric. One of the pump processor and the certification application processor can be further configured to verify that the at least one operating parameter is within the specified operating metric. In some cases, the certification application comprises a user interface for displaying information relating to the certification application and allowing user interaction with the certification application. In some cases, the certification application further comprises a memory for storing at least one of the instructions and information relating to the certification application. In some cases, the certification application comprises instructions to identify the specified operating metric.

Figure 2:
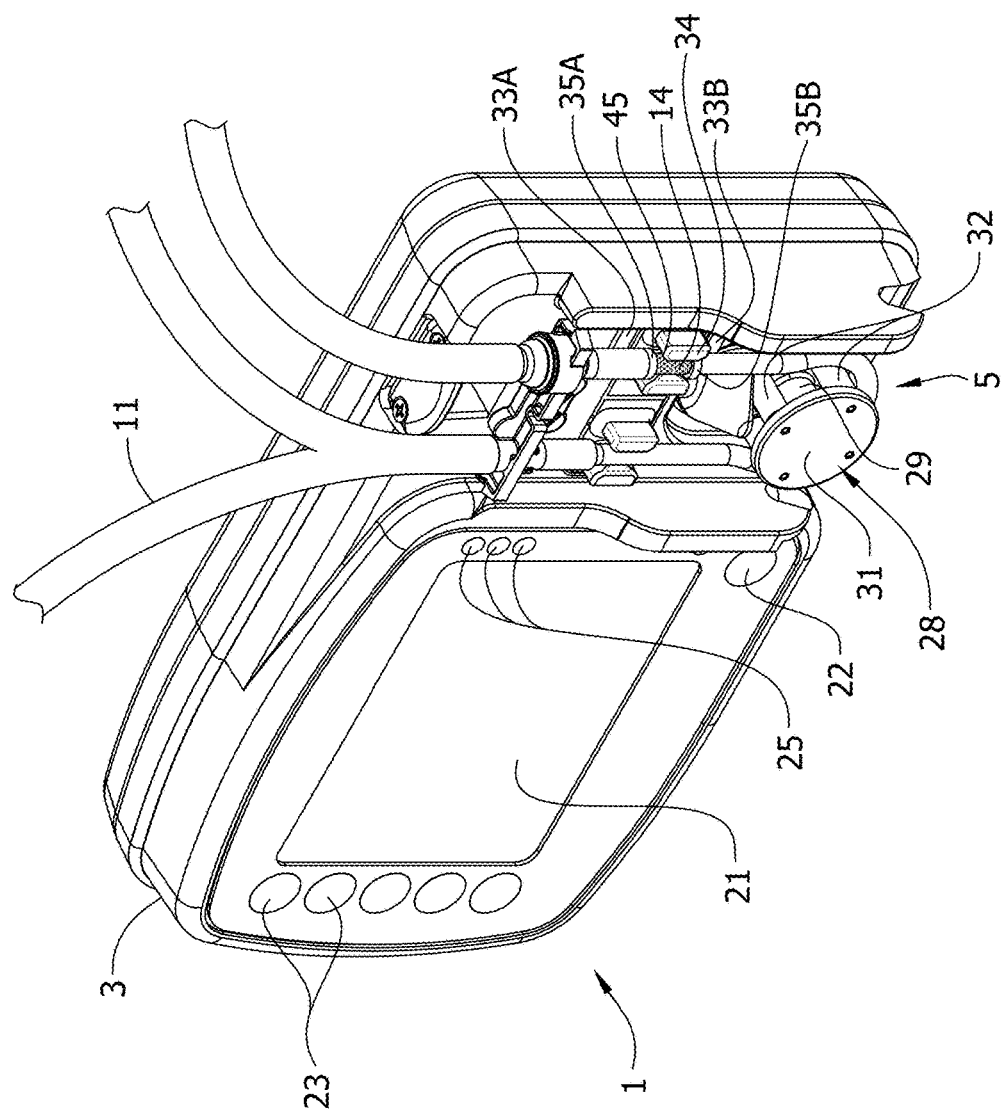
FIG. 2 is a perspective of FIG. 1 with a cassette housing of the feeding set removed.
Figure 3:
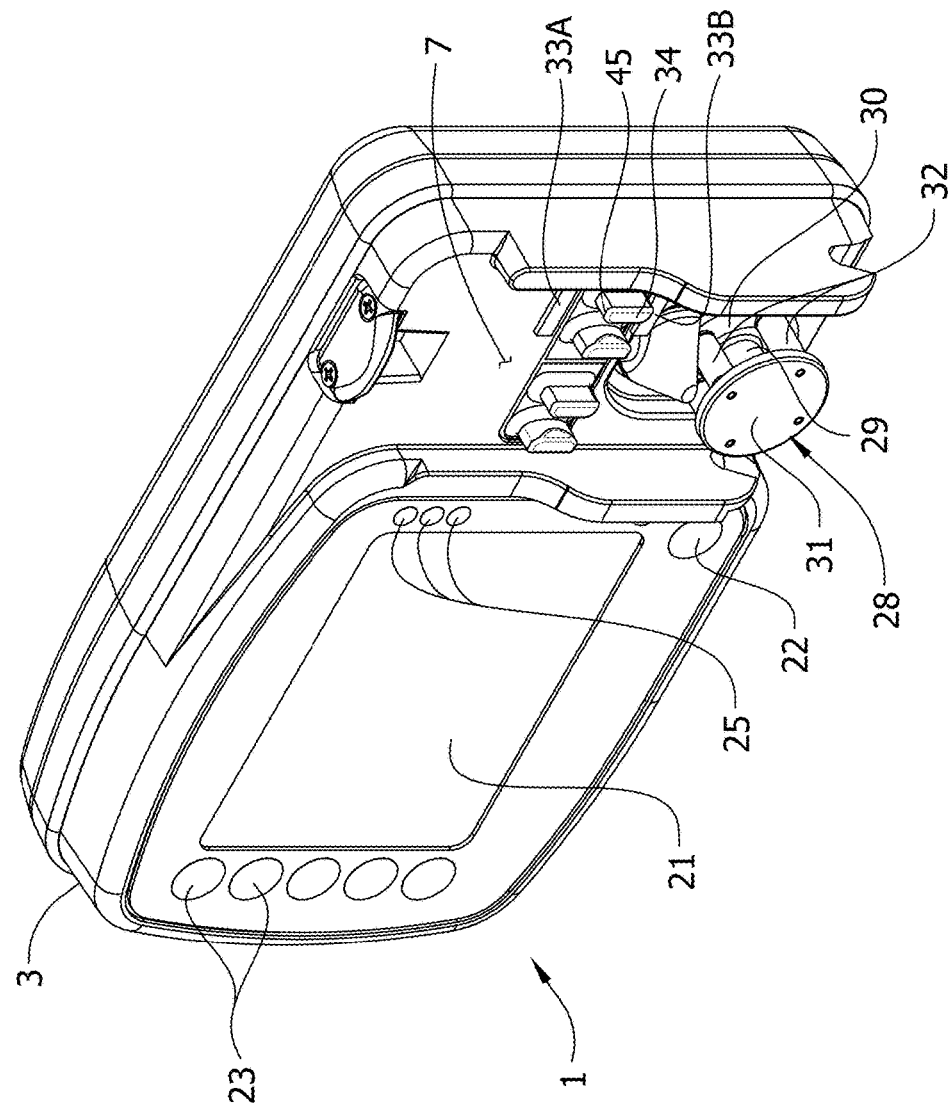
FIG. 3 is the perspective of FIG. 1 with the feeding set removed.

Referring now to the exemplary embodiment schematically illustrated in FIGS. 1-3, an enteral feeding pump is generally indicated at 1. The pump 1 may comprise a housing 3 that is constructed so as to allow an administration feeding set 5 to be mounted to the housing. The housing 3 may comprise a recess 7 (FIG. 3) for receiving a cassette 9 of the feeding set 5 to load the feeding set on the pump. The administration feeding set 5 can comprise tubing indicated generally at 11 that provides a fluidic pathway between a bag 12 of nutritional liquid and a patient (FIG. 1). The bag 12 is shown schematically in FIG. 1. The cassette 9 may mount the tubing 11 for engaging the tubing with the pump 1 when the cassette is received in the recess 7. It will be understood that the pump and feeding set may have over configurations within the scope of the present invention.

Figure 4:
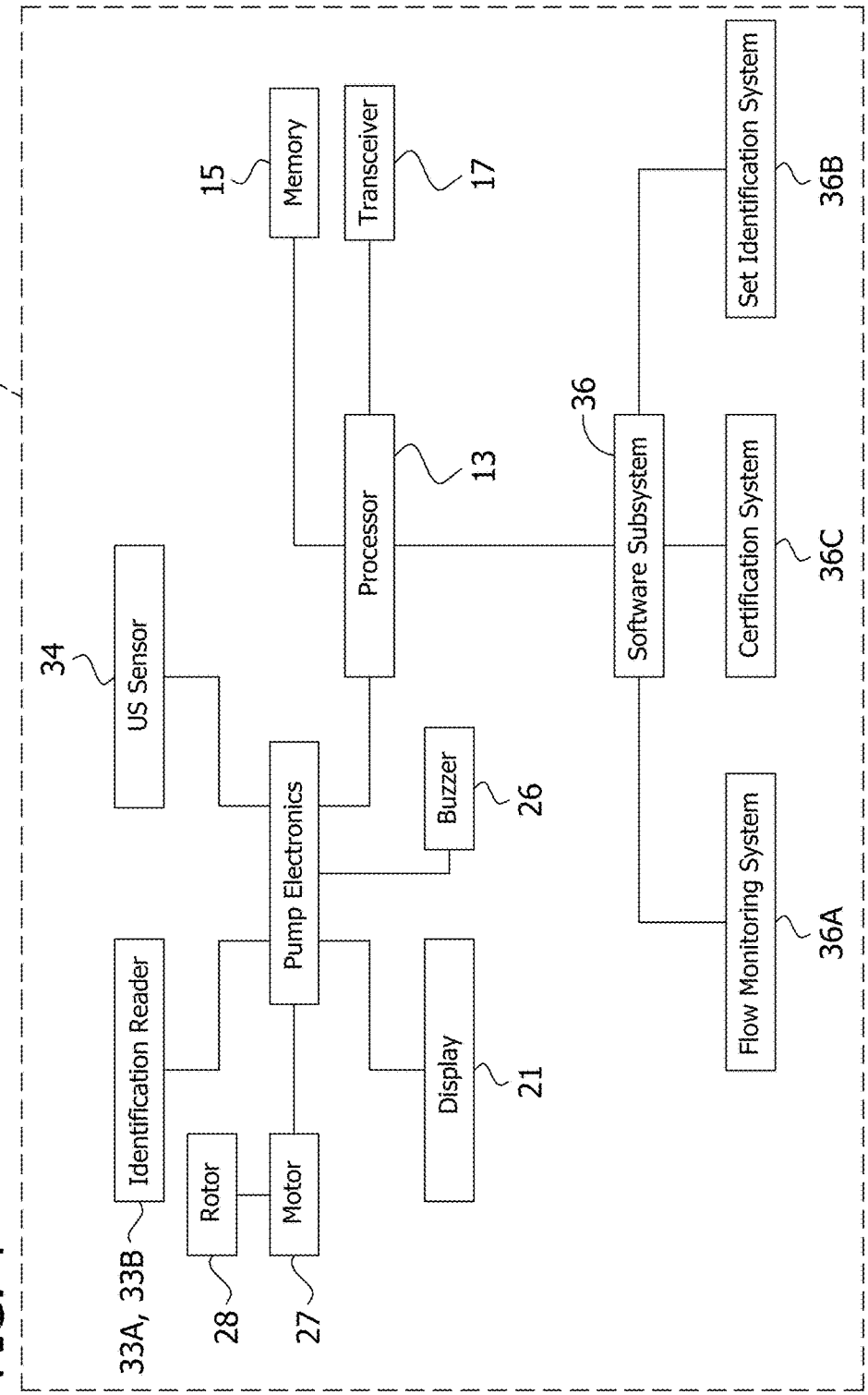
FIG. 4 is a block diagram schematically illustrating the pump.

Referring to FIG. 4, a processor 13 may be programmed to control operation of the pump 1 to deliver nutritional liquid through the feeding set 5 and to a patient. As will be explained in detail below, the processor 13 is configured to monitor and determine various parameters and components of the pump 1 during operation of the pump. The processor 13 may be operatively associated with memory 15 for storing the determined parameters and components. A transceiver 17 may be operatively associated with the processor 13 for transmitting the determined parameters and components to a remote location and/or receiving information from a remote location facilitating verification that the parameters and components of the pump 1 are functioning within a predetermined operational range. Broadly, the predetermined operational range may be a specified operating metric of the parameter/component. To this effect, remote certification of the pump 1 can be performed.

As used herein, the term "load" means that the tubing 11 is engaged with the pump 1 so that the administration feeding set 5 is ready for operation with the pump to deliver fluid to a patient. It will be appreciated that the term "housing", as used herein, may include many forms of supporting structures including, without limitation, multipart structures and structures that do not enclose or house the working components of the pump 1.

The pump 1 may include a user interface with a display screen indicated at 21 on the front of the housing that is capable of displaying information about the status and operation of the pump (FIG. 1). Power button 22 can turn the pump 1 on and off. The pump 1 can further comprise buttons 23 and light emitting diodes 25 on the housing 3 for use with the display screen 21 to facilitate exchanging information, such as providing and obtaining information, between the pump 1 and a user. The light emitting diodes 25 may comprise separate red, yellow, and greed LEDs. A buzzer 26 (FIG. 4) may provide an auditory signal for various operations of the pump. Various user interfaces for displaying information to the user and receiving user input may be implemented. Any of the various configurations of the user interface can involve utilizing one or more graphical display subcomponents. As an example, the display screen 21 may be a graphical user interface having a touch screen by which the user can provide the input information. In other embodiments, the user interface can be a tethered component that can be used to provide input information, provide operating information pertaining to the flow control apparatus, or both.

Referring to FIGS. 2-4, the pump 1 may include a pump motor 27 (FIG. 4) located in the housing 3. A pump rotor 28 may be mounted on a rotatable shaft 29 and rotated by the motor 27. In one embodiment, the pump rotor 28 includes an inner disk 30, an outer disk 31, and preferably a plurality of rollers 32 mounted between the inner and outer disks rotatable about their longitudinal axes relative to the disks. In the exemplarily illustrated embodiment, the pump motor 27, rotatable shaft 29 and pump rotor 28 may broadly be considered a pumping device. The rollers 32 may engage the administration feeding set 5 for moving fluid through the feeding set for delivery to a patient.

The motor 27 may draw current from a power source (not shown) to turn the rotor 28. The current draw of the motor 27 may vary with its load. Thus, when a feeding set is loaded on the pump 1, the tubing 11, in compressed engagement with the rotor 28, may increase the load on the motor 27. Preferably, a properly functioning motor 27 will draw a consistent current under consistent load conditions, e.g., when no feeding set is loaded.

Pump electronics of the pump 1 may also include identification readers 33A, 33B, the display 21, the motor 27, and an ultrasonic sensor 34. The processor 13 in the housing 3 controls the pump electronics and uses the memory 15. A software subsystem 36 is shown schematically separate from the memory 15, and includes a flow monitoring system 36A, a set identification system 36B capable of identifying the type of set mounted on the pump 1, and a certification system 36C, the operations of which will be described more fully hereinafter. Other pump electronics can include an accelerometer (not shown) for detecting motion of the pump 1.

To detect flow conditions in a downstream portion of the tubing 11, the ultrasonic sensor 34 is configured for alignment with the downstream portion of the tubing 11. In the illustrated embodiment, the sensor 34 is positioned in the recess 7 and is adapted to receive the tubing 11 therein when the feeding set 5 is loaded on the pump 1. The ultrasonic sensor 34 may be configured to produce a signal representative of the pressure buildup (or fluid flow) in the downstream portion of the tubing 11. In combination with the processor 13 and the flow monitoring subsystem 36A of software subsystem 36, the ultrasonic sensor 34 may be configured to alert to an undesirable flow condition in the downstream portion of the tubing 11.

As shown best in FIG. 2, a mounting member 14 is configured to engage a mount 45 of the pump 1 when the feeding set 5 is loaded thereon. Optional readers 33A, 33B disposed on or within the pump 1, may detect the presence of respective identification members 35A, 35B attached to the feeding set 5. Preferably, the identification members 35A, 35B may be configured to be aligned with respective ones of the readers 33A, 33B when the feeding set 5 is loaded on the pump 1. Upon engagement of the mounting member 14 to the mount 45, readers 33A, 33B may be capable of sensing the identification data represented by the number and position of the identification members 35A, 35B. In combination with the processor 13, memory 15, and software subsystem 36, the readers 33A, 33B and the identification members 35A, 35B may identify at least one characteristic of the nutritional liquid associated with the feeding set 5 loaded on the pump 1. Additionally, they may provide a signal representative of proper alignment when the cassette 9 is properly loaded into the housing 3. The set identification subsystem 36B allows the pump 1 to identify that a certification set has been loaded, and to configure itself for operating in a configuration mode.

As discussed above, the pump 1 includes several features that may be used to ensure consistent and accurate delivery of nutritional or medicinal solutions to patients (e.g., the identification readers 33A, 33B, the ultrasonic sensor 34, motor current, power button 22, buttons 23, LEDs 25, buzzer 26, accelerometer, etc.). Many of these features, as well as other features of the pump 1, can be certified on occasion for the health and safety of the patient to determine whether the pump is functioning within a predetermined operational range. It will be understood that not all of these features, or other unnamed features could be present within the scope of the invention.

During use, the processor 13 can send instructions to monitor the pumping parameters and intermittently, continuously, or continually adjust the instantaneous operating flow rate for the pump 1 to achieve a target feeding rate. For instance, the processor 13 may keep track of the volume of feeding fluid delivered to the patient, and the number of calories delivered to the patient. Other feeding parameters, such as but not limited to elapsed time, remaining time, and fat content delivered, may also be monitored and optionally displayed through, for example, the user interface. The processor 13 may keep track of other flow parameters of the pump 1 as well as parameters of the pump not directly associated with fluid flow.

Similar to the pump electronics, a certification of the monitored pumping parameters (i.e., volume of fluid delivered, number of calories delivered, etc.) can be performed by comparing the monitored pumping parameters to target pumping parameters to assess whether the target pumping parameters are being met and/or a prescribed treatment regimen is being followed. Results of the comparison can be stored in the memory 15 for review by the clinician. The data can also be stored in the memory 15 for wireless data mining, service modules, and/or asset tracking purposes.

Figure 5A:
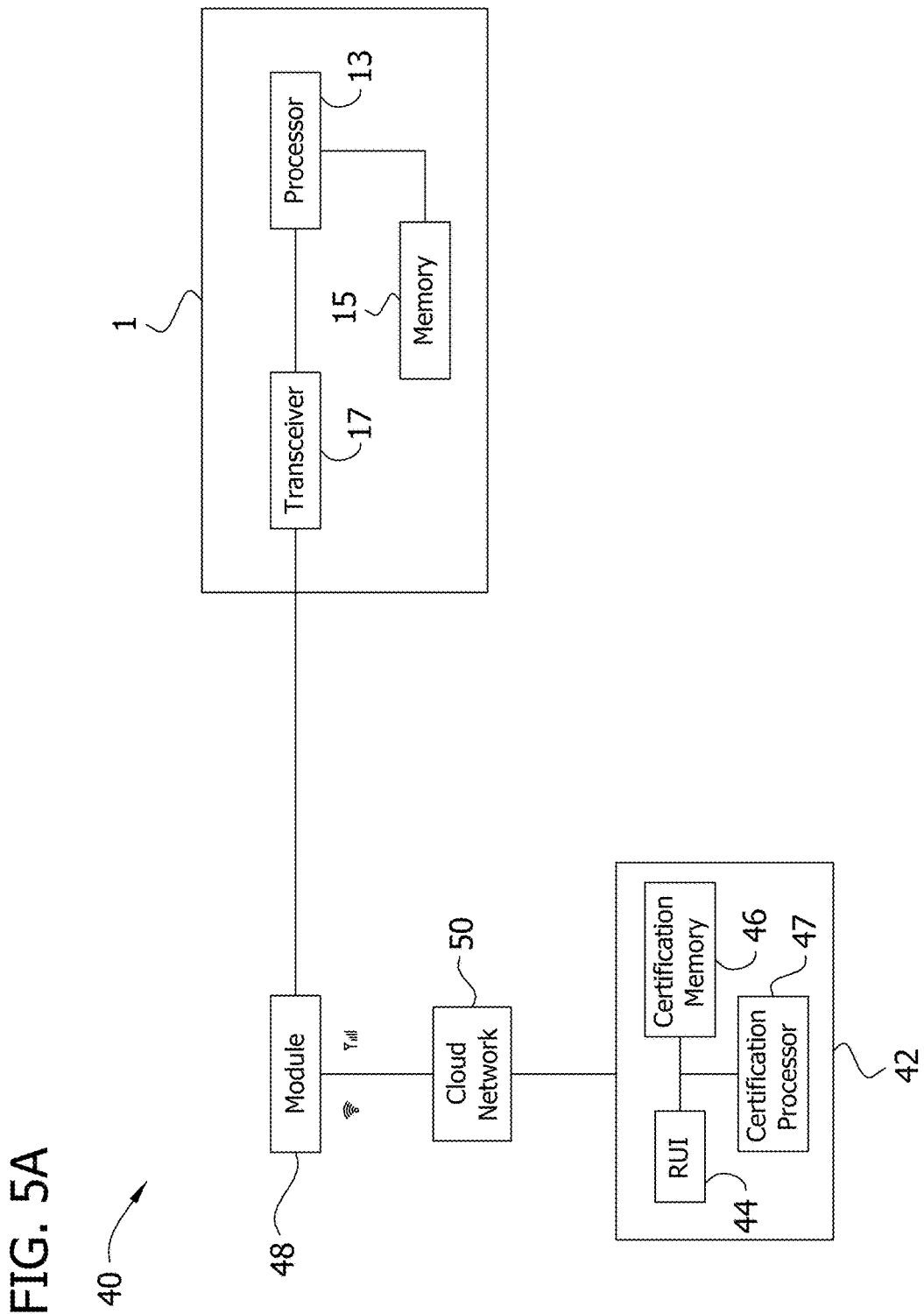
FIG. 5A is a block diagram schematically illustrating a certification system.

Referring to FIG. 5A, a certification system 40 can be used to perform a certification on the pump 1 to verify that certain parameters and components of the pump 1 are functioning within predetermined operational ranges. The transceiver 17 is in operative communication with the processor 13 for wirelessly transmitting information retrieved by the processor, such as from memory 15, pertaining to various parameters and components of the pump 1. The transceiver 17 may comprise a ZIGBEE radio mounted on a printed circuit board (not shown) of the pump 1. The components of the ZIGBEE radio are known by a person having skill in the art and thus will not be described in detail. It should be understood that the ZIGBEE radio may be contained within or disposed external to pump 1. The transceiver 17 may also be configured for sending a transmission across a wired connection.

ZIGBEE networks based on the IEEE 802.15.4 standard for wireless personal area networks have been used for collecting information from a variety of medical devices in accordance with IEEE 11073 Device Specializations for point-of-care medical device communication. See, e.g., *ZIGBEE Wireless Sensor Applications for Health, Wellness and Fitness*, the ZIGBEE Alliance, Mar. 2009, which is incorporated by reference herein in its entirety. ZIGBEE networks provide the advantage of being dynamically configurable, for example, in "self-healing" mesh configurations, and operating with low power requirements (enabling, for example, ZIGBEE transceivers to be integrally coupled to the medical devices under battery power). However, transmission ranges between individual ZIGBEE transceivers are generally limited to no more than several hundred feet. The wireless relay network or additional wireless relay networks may be organized according to a variety of other wireless local area network (WLAN) or WPAN formats including, for example, WiFi WLANs based on IEEE 802.11 and BLUETOOTH WPANs based on IEEE 802.15.1.

For compliance with HIPAA regulations, the wireless communication is preferably conducted securely using, for example, encryption, a Secure Socket Layer (SSL) protocol, or a Transport Layer Security (TLS) protocol.

A remote certification application 42 may communicate with the pump 1 through the transceiver 17 to receive the pump information transmitted by the transceiver. The certification application 42 can facilitate analysis of the received information to verify that the parameters and components of the pump 1 are functioning properly, within a predetermined operational range. The certification application 42 may comprise a remote user interface (RUI) 44 for displaying information regarding the certification application 42 and allowing user interaction with the certification application, a certification memory 46 in communication with the remote user interface for storing information regarding the certification application, and a certification processor 47 for controlling operation of the certification application. A module 48 may be in communication with the transceiver 17 of the pump 1 and configured to transmit the certification information to a cloud network 50, which can transmit the certification information to the certification application. The cloud network 50 can be accessed by the module 48 to send updates regarding the certification application 42 and send data or commands to the pump 1 regarding the certification system 40 as well as updates regarding general pump operation.

In another embodiment, the module 48 may be in direct communication with the certification application 42 (FIG. 5B) for transmitting information pertaining to the certification application between the pump 1 and the certification application. The certification system 40 can also include multiple modules 48 for communicating with multiple devices. Also, multiple pumps 1 can be included in the certification system 40. The pumps (via the transceivers) and modules can be arranged in a mesh network within a patient facility. The pumps and modules could be configured to communicate with one another via associated wireless links. The network could be a ZIGBEE mesh network based on IEEE 802.15.4. However, the network may be organized according to a variety of other wireless local area network (WLAN) or WPAN formats including, for example, WiFi WLANs based on IEEE 802.11 and BLUETOOTH WPANs based on IEEE 802.15.1.

Figure 5C:
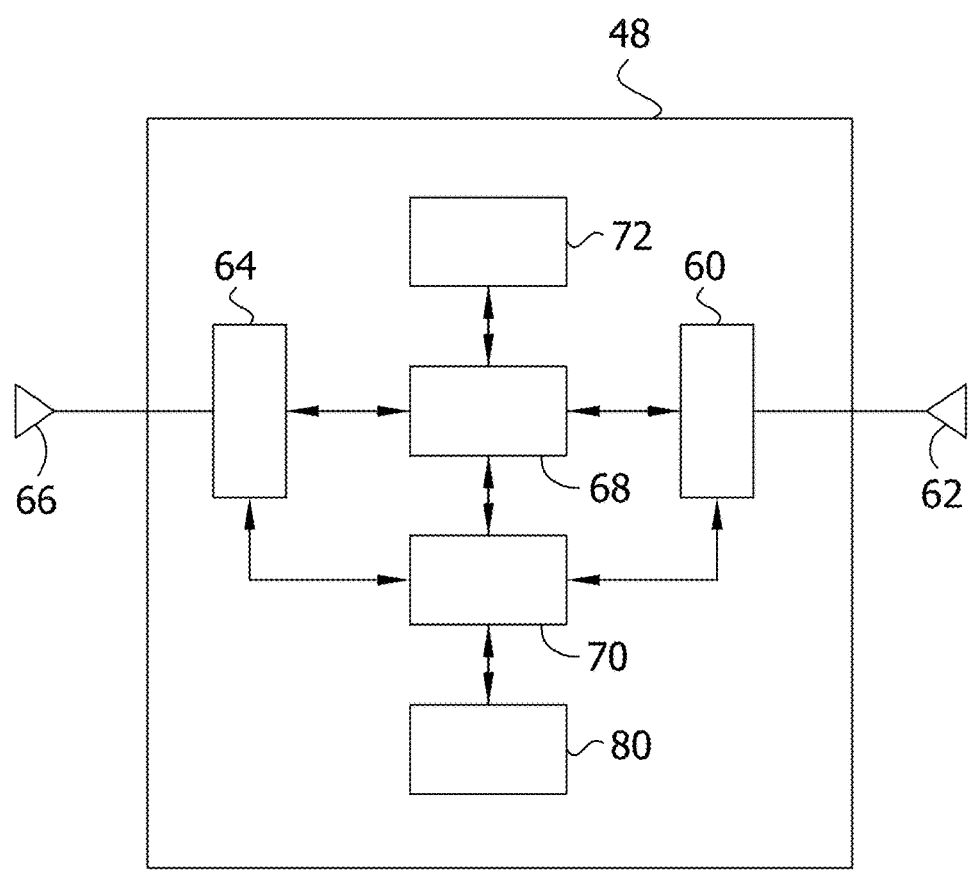
FIG. 5C is a block diagram schematically illustrating a module of the certification system.

FIG. 5C provides a block diagram illustrating exemplary components of module 48. The module 48 is configured to receive a ZIGBEE radio signal from the transceiver 17 and transmit a WiFi or cellular signal to the certification application 42 or other location (e.g., cloud network 50) for communicating information between the pump 1 and certification application 42. The module 48 includes a first transceiver 60 for wirelessly communicating with transceiver 17 of the pump 1 via an antenna 62 and a second transceiver 64 for wirelessly communicating with the cloud network 50 via an antenna 66. Each of the transceivers 60, 64 is in communication with a data processing circuit 68, which is configured to operate under the control of a controller, e.g., processor, 70 to accept data received by the transceivers 60, 64 and store the received data in a memory such as buffer element 72. In addition, the data processing circuit 68 is further configured to retrieve data from the buffer element 72 under the direction of the processor 70, and provide the retrieved data to a selected one of the transceivers 60, 64 for transmission.

The processor 70 is also preferably in communication with an input/output circuit 80, which provides signals to one or more display elements of the module 48, for example, for indicating a start-up or current status of the module 48, including communication or connection status with the certification application 42 or the cloud network 50. Input/output circuit 80 may also be configured to provide signals to indicate an A/C power loss, and or to be responsive to signals provided by one or more input devices provided in proximity to the one or more display elements.

The module 48 may preferably be provided as a small physical enclosure with an integral power plug and power supply circuit, such that the module may be directly plugged into and supported by a conventional wall outlet providing commercial A/C power. The module 48 may also preferably include a battery back-up circuit (not shown) to provide uninterrupted power in the event of A/C power outage of short duration. Battery back-up may also be advantageous, for example, for using the module 48 in an ambulatory mode that enables the patient to move within and potentially at a distance from a treatment location, for example, with a pump 1 that is a portable feeding device. In this configuration, for example, the pump 1, the transceiver 17, and module 48 may be conveniently carried in a patient-wearable backpack. It will be understood that the module can be configured other than described herein within the scope of the present invention.

The certification system 40, through the certification application 42, may be configured to perform various certification protocols on the pump 1. For instance, the certification application 42 can perform a remote certification protocol on the pump 1 to remotely verify that certain parameters and components of the pump 1 are functioning properly, within predetermined operational ranges. The parameters of the pump 1 can include but are not limited to, the identification readers 33A, 33B, the ultrasonic sensor 34, motor current, power button 22, buttons 23, LEDs 25, buzzer 26, accelerometer, set presence reading, accuracy, rotor encoder(s), ultrasonic voltage and frequency, other voltages, and fluid delivery pumping parameters (i.e., volume of fluid delivered, number of calories delivered, etc.).

Figure 6A:
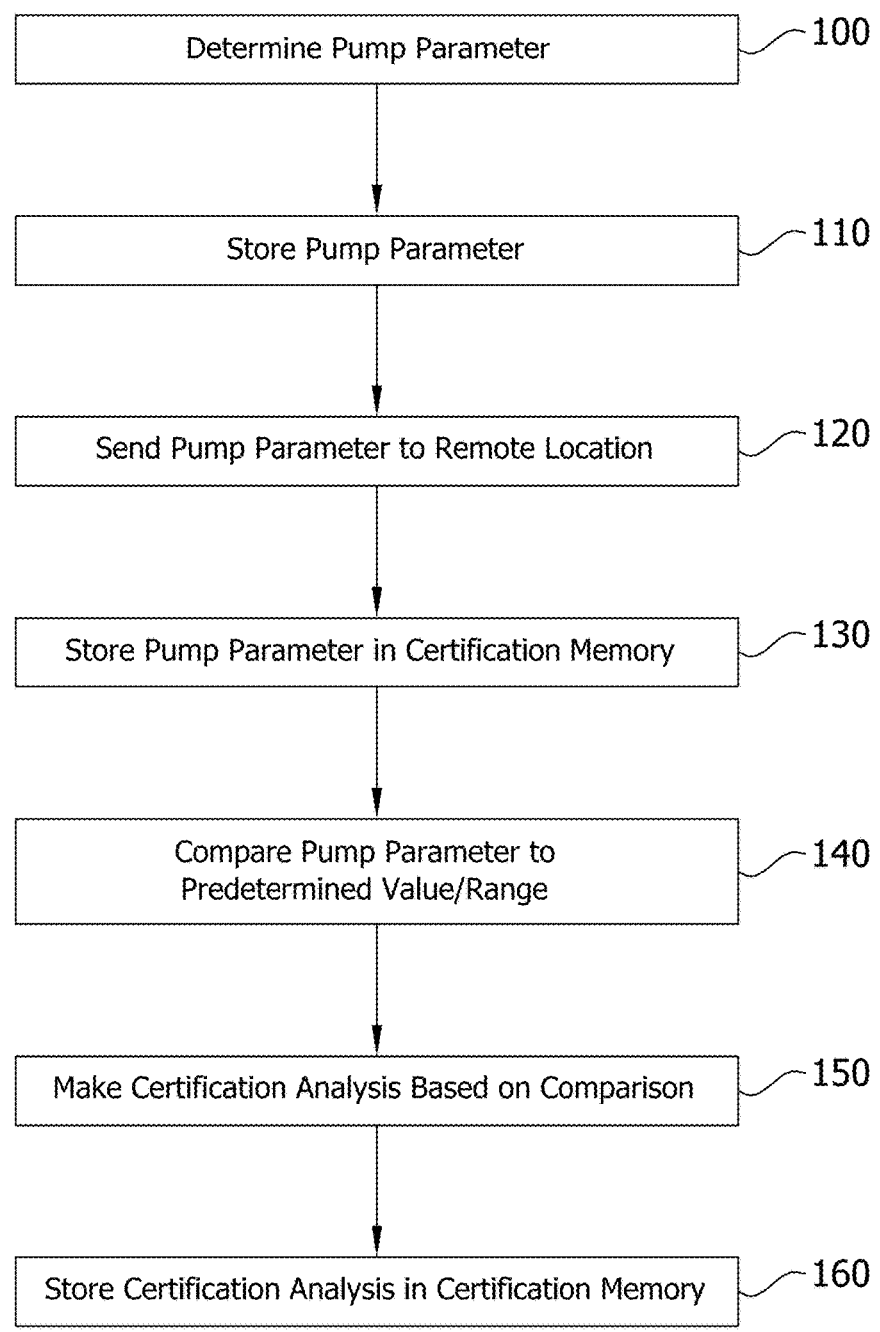
FIG. 6A is a flow chart of a remote certification routine.

Referring to FIG. 6A, in the remote certification protocol, at 100, the pump 1 determines at least one pump parameter of the pump. The pump parameter can be determined during operation of the pump 1 to supply nutritional liquid to a patient. At 110, the pump 1 stores the at least one pump parameter in the memory 15 of the pump. At 120, the pump 1 sends the at least one pump parameter to the certification application 42. This can be done at predetermined intervals, and/or at the request of support personnel using the certification application 42. The pump information is sent between the pump 1 and the certification application 42 via the wireless communication between the transceiver 17, module 48, and cloud network 50. At 130, the determined pump parameter is stored in the certification memory 46 of the certification application 42 along with a date and time stamp of when the pump parameter was determined. At 140, the determined value of the pump parameter is then compared to a predetermined acceptable range/value for the parameter stored in the certification memory 46. At 150, a certification analysis of the pump parameter is completed classifying the pump parameter as either passing or failing certification, and at 160, the results of the analysis can be stored in the certification memory 46. The result could also be transmitted back to the pump 1. In this instance, the comparison of the pump parameters and components is performed by the certification application 42.

Figure 6B:
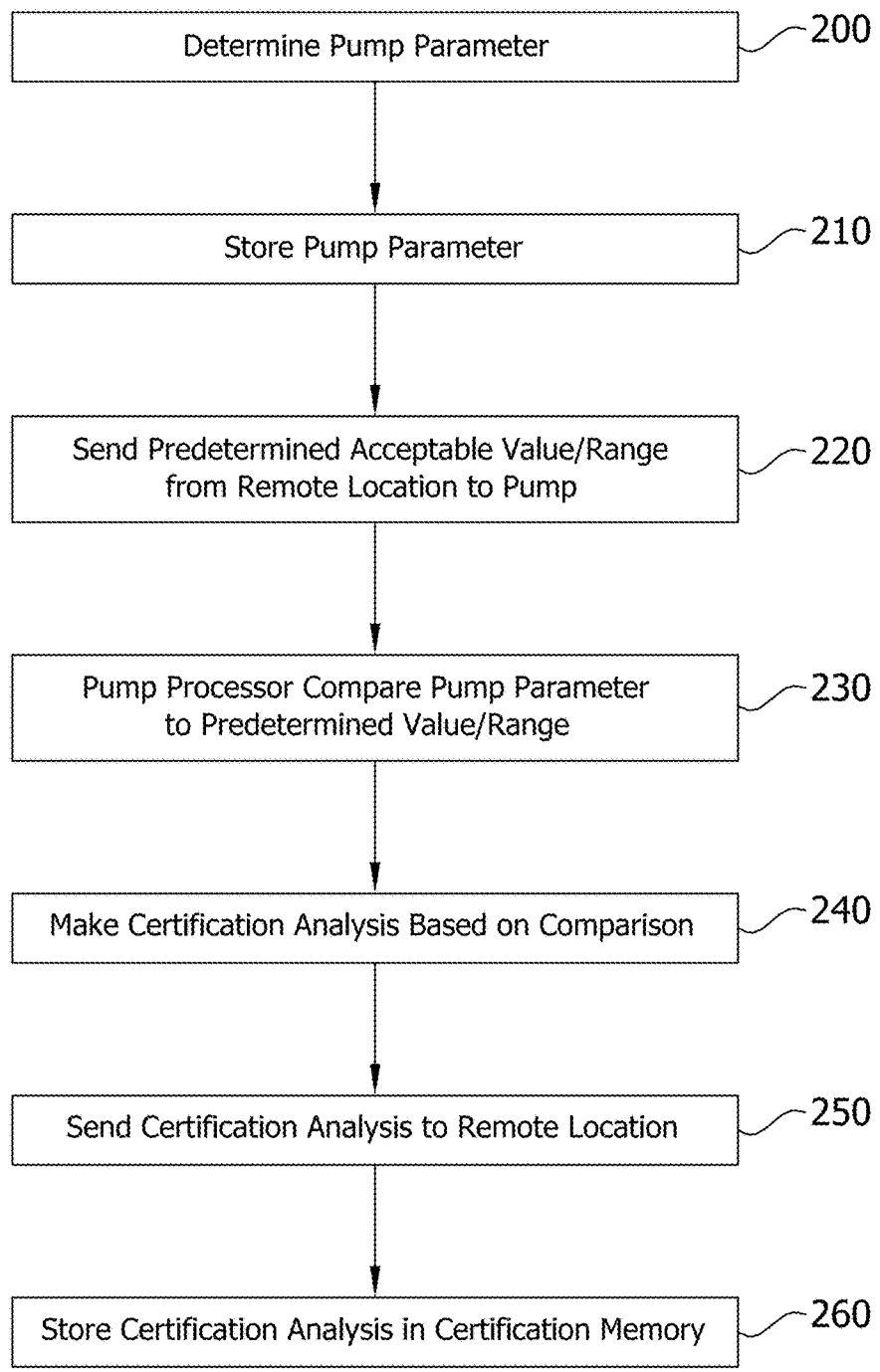
FIG. 6B if a flow chart of another remote certification routine.

Referring to FIG. 6B, the comparison of the pump parameters and components can also be performed by the processor 13 of the pump 1. If the comparison is performed by the processor 13, at 200, the pump 1 determines at least one pump parameter of the pump. The pump parameter can be determined during operation of the pump 1 to supply nutritional liquid to a patient. At 210, the pump 1 stores the at least one pump parameter in the memory 15 of the pump. At 220, the certification application 42 sends the predetermined acceptable range/value of the pump parameter to the processor 13 via the module 48, cloud network 50, and transceiver 17, and, at 230, the processor uses the received range/value to perform the comparison. At 240, a certification analysis of the pump parameter is completed by the processor 13. At 250, the results of the analysis can be sent to the certification application 42, and at 260, the results can be stored in the certification memory 46. The certification results can also be stored in the memory 15 of the pump 1.

Whether the comparison is performed by the certification application 42 or the processor 13 of the pump 1, the certification system 40 completes a remote certification test on the pump 1 by communicating the pump with the certification application during the certification routine. Moreover, the certification test is performed without replacing the administration feeding set 5 with a certification feeding set. This allows certification to be performed on the pump 1 wherever the pump is currently in use in the field so that support personnel do not have to retrieve the pump from the field, which interferes with patient treatment. In addition, because the pump 1 stores the determined pump parameters and components in the memory 15, and the memory is in communication with the certification application 42, a certification routine can be performed at any time. This effectively creates a "continuous certification" feature whereby certification can be performed on demand. The "continuous certification" feature also permits the pump 1 to assess a certification status for a certain pump parameter and instruct a user to initiate a full certification procedure if the assessed certification status it outside of a specified operating metric for the pump parameter. In some cases, at least one processor is configured to send a signal recommending performing certification on each of the at least one operating parameter if the processor evaluates that at least one operating parameter is outside of the specified operating metric.

If the certification system 40 determines that at least one or all the compared parameters and components are within the predetermined acceptable ranges, the certification application 42 can identify which of the parameters and components passed certification. A certification page (i.e. a text display) showing the pump certification can be displayed on the remote user interface for printing and/or saving to the certification memory 46. The certification page can include a serial number of the pump for recording the certification in association with the particular pump. A certification date can also be saved in the certification memory 46.

Figure 7:
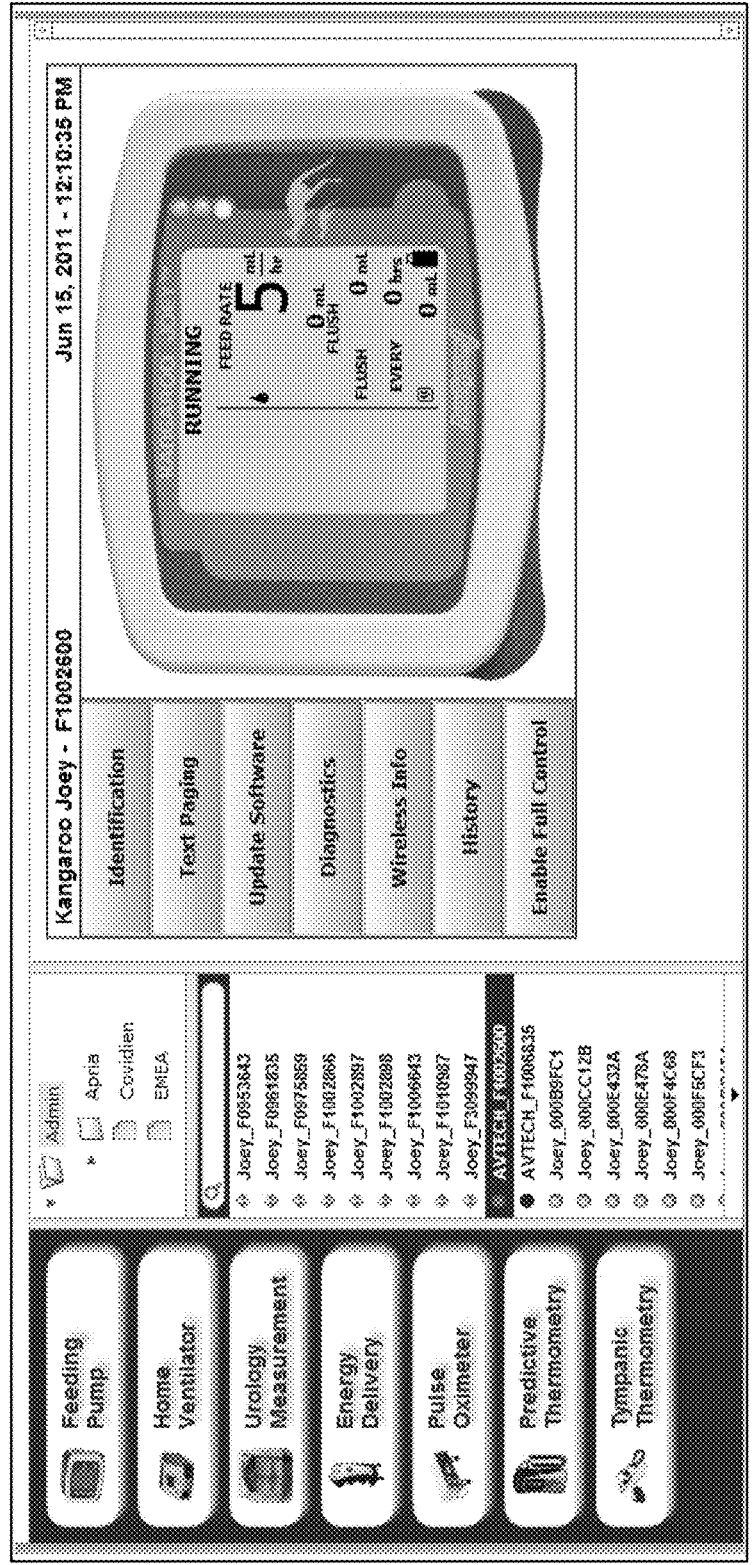
FIG. 7 is an exemplary display generated by a certification application of the certification system emulating a display of the pump.
Figure 8:
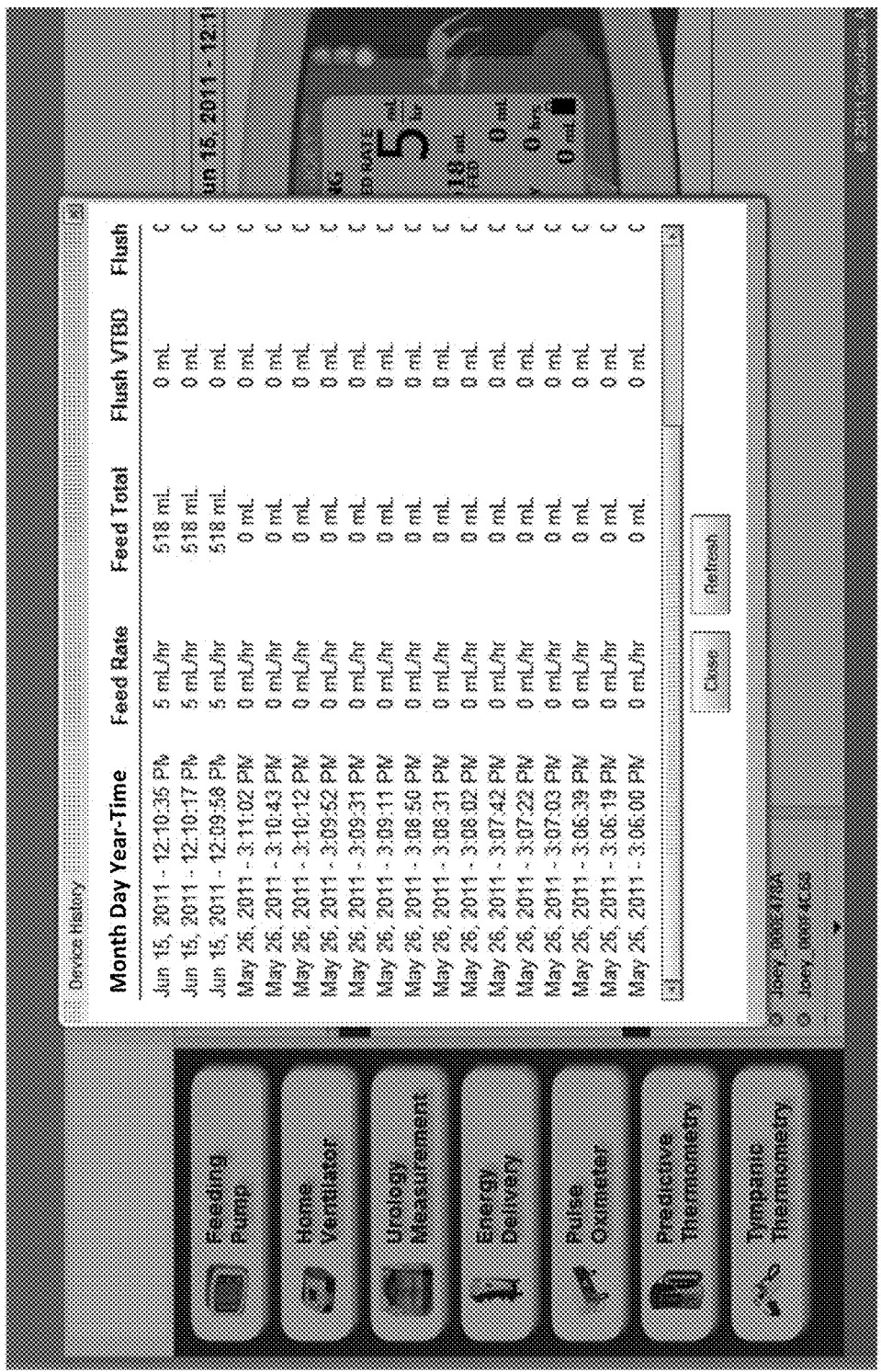
FIG. 8 is an exemplary display generated by the certification application showing a feed and flush data table over a selected period of time.
Figure 9:
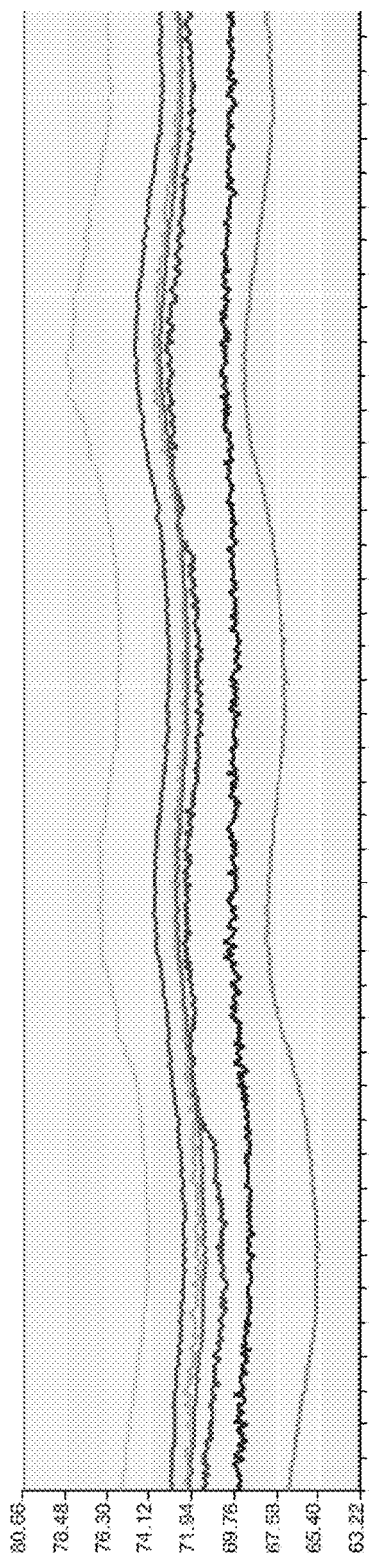
FIG. 9 is an exemplary graph generated by the certification application illustrating feed and flush data over a period of time.

The remote certification protocol can operate in parallel with various operational modes of the certification system 40. During a monitor mode, the certification system 40 provides a real time wireless connection between the certification application 42 and the pump 1 so that support personnel using the certification application may remotely connect to the pump for at least one of diagnostic, troubleshooting, and training purposes. The remote user interface 44 may also display an emulation of what is being displayed on the display screen 21 of the pump 1. An example of the remote user interface 44 displaying an emulation of the pump display screen 21 is shown in FIG. 7. The remote user interface 44 replicates the pump display screen 21 showing the most recent data received from the pump 1. During diagnostic and troubleshooting operational modes of the certification system 40, the pump 1 updates the certification application with typical use and diagnostic use parameters and components periodically and/or upon request from support personnel. Using the remote user interface 44, a support personnel user may graph the parameters and components to ascertain a level of the pump's performance within predetermined ranges (i.e., verify pump certification). In one instance, updating the certification application 42 with typical use data may include sending information from the pump 1 to the certification application regarding the amount of fluid delivered to a patient. FIG. 8 illustrates an exemplary display of the remote user interface 44 showing a feed and flush data table over a selected period of time. FIG. 9 illustrates an exemplary feed and flush graph that can be displayed on the remote user interface 44. The remote user interface 44 may also generate a message reporting the data sent from the pump 1.

Figure 10:
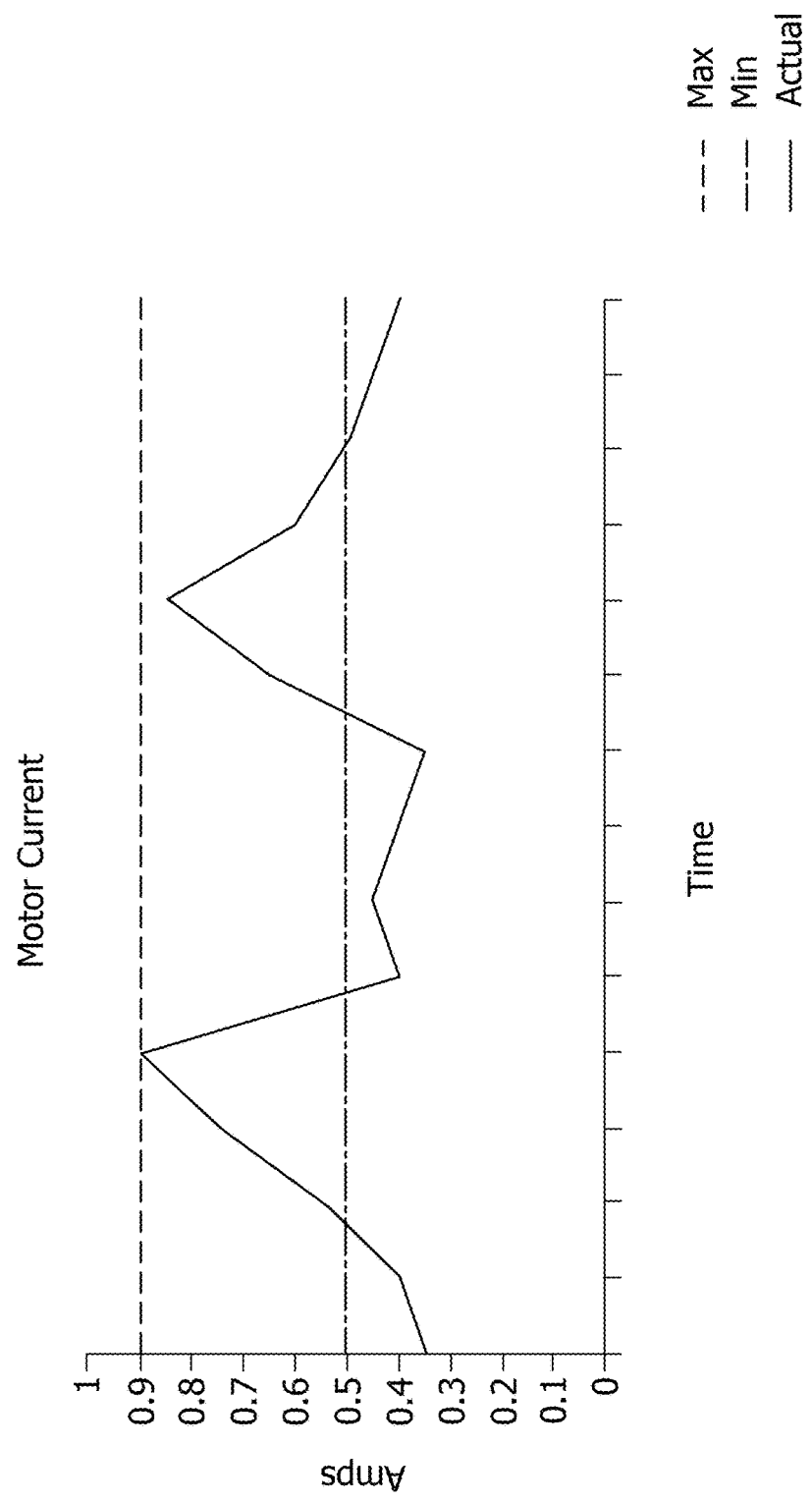
FIG. 10 is an exemplary graph generated by the certification application illustrating motor current over time.

FIG. 10 shows a graph of motor current over time, which can be displayed on the remote user, interface 44 during a diagnostic assessment. Graphs and charts may be generated for any diagnostic parameter for a given time and date. The graphs and charts may also be exported for use in other database applications. Messages regarding troubleshooting may be initiated upon request of support personnel and may transmit data every 15 seconds for 10 minutes to assess a particular problem area of the pump 1. Other time intervals may also be used. When support personnel initiate a retrieve pump data now request, the pump 1 sends any status and diagnostic messages reporting the pump data that are available at the time of the request. This data request can be performed during the monitor mode. Messages regarding software upgrades may be transmitted along with any scheduled or requested transmission. All messages, notifications, tables, and graphs can be saved in the certification memory 46 of the certification application 42.

The certification application 42 may also store cellular numbers in the certification memory 46 and transmit status and error messages to a selected cellular phone via the module 48.

The certification system 40 can also perform a manual certification protocol where a user or support personnel manually operates the pump 1 to conduct the certification. The manual certification protocol can be initiated at the pump 1 or at the remote user interface 44 by sending a command to the transceiver 17 instructing the pump to perform the certification functions for obtaining values of certain pump parameters and components. However, a user must manually operate the pump through this process. The obtained pump parameters and components can be transmitted to the certification memory 46 of the certification application 42 along with a date and time stamp. The comparison of the pump parameters and components can be performed by the processor 13 of the pump or by the certification application 42. If the comparison is performed by the processor 13, the results can be sent to the certification application 42 and stored in the certification memory 46. The manual certification protocol can also be initiated in response to a determination by one of the processor 13 or certification application 42 that a determined pump parameter is outside of the predetermined acceptable range/value for the pump parameter. A certification date can be saved in the certification memory 46. If a manual certification is initiated and the certification system 40 determines that sufficient data for the pump parameters and components is already stored in one of the memory 15 of the pump 1 or the certification memory 46, the system can initiate a certification protocol without running the pump through the manual certification routine.

The certification system 40 can also perform a factory certification protocol (broadly, an initial certification) where, after manufacturing, a user logs into the remote user interface 44 and sends a pump serial number for a pump to the remote user interface to link the pump with the certification application 42. The serial number is then stored in the certification memory 46 and a manual certification as previously explained is conducted. The factory certification protocol can be used to load initial acceptable ranges and values for certain parameters and components of the pump for use during subsequent certification protocols. A date of the factory certification can be stored in the certification memory 46. Additionally, when the pump 1 is powered on, the certification application 42 can recognize the pump by the serial number and identify the pump as active for certification purposes. To do so, a user enters the pump serial number into the remote user interface 44 and the serial number is checked against known serial numbers stored in the certification memory 46, such as the serial numbers stored during the factory certification. The connection between the pump 1 and certification application 42 are indicated as valid if the pump serial number can be found in the certification memory.

In some configurations, if a user of the remote application attempts to obtain a pump certification determination, the remote application looks back at data gathered over a predetermined past period, e.g., over the last 10 days, from the pump. For each parameter, the remote application will look at the most recent point gathered in that time; if the last value was out of range, the parameter will fail but if the last value was a pass, the parameter will pass. If the remote application has no data for that parameter over the period, e.g., the last 10 days, the parameter will be indeterminate (unknown). Indeterminate results are typically caused by the pump not being actively used. Manual certifications are typically required only if the result of one or more parameters as stored in the remote certification is failed or indeterminate.

It is to be understood that in the described embodiment, the software subsystem 36, the processor 13, memory 15, and the certification application 42 may be broadly considered "a control circuit". These components may also be individually considered "a control circuit". Moreover, other types of control circuits may be used within the scope of the present invention.

The memory 15 and certification memory 46 can comprise one or more non-volatile memory components, e.g., ROM, PROM, EPROM, EEPROM, and flash memory. In other configurations, other types of non-volatile memory components can be utilized in addition to or instead of the non-volatile memory components such as but not limited to removable or portable data storage devices, such as hard disk drives, optical disk, magnetic tape, holographic memory, and memory cards. Alternatively or in addition, memory 15 and certification memory 46 can comprise one or more volatile memory components such as but not limited to random access memory (RAM), dynamic random access memory (DRAM), and static random access memory (SRAM).

Embodiments of the invention may be described in the general context of computer-executable instructions, such as program modules, executed by one or more computers or other devices. The computer-executable instructions may be organized into one or more computer-executable components or modules including, but not limited to, routines, programs, objects, components, and data structures that perform particular tasks or implement particular abstract data types. Aspects of the invention may be implemented with any number and organization of such components or modules. For example, aspects of the invention are not limited to the specific computer-executable instructions or the specific components or modules illustrated in the figures and described herein. Other embodiments of the invention may include different computer-executable instructions or components having more or less functionality than illustrated and described.

Further, the order of execution or performance of the operations in embodiments of the invention illustrated and described herein is not essential, unless otherwise specified. That is, the operations may be performed in any order, unless otherwise specified, and embodiments of the invention may include additional or fewer operations than those disclosed herein. For example, it is contemplated that executing or performing a particular operation before, contemporaneously with, or after another operation is within the scope of aspects of the invention.

In operation, the processor 15, certification processor 47, and module processor 70 execute computer-executable instructions such as those illustrated in the figures to implement aspects of the invention. Aspects of the invention may also be practiced in distributed computing environments where tasks are performed by remote processing devices linked through a communications network. In a distributed computing environment, program modules may be located in both local and remote computer storage medium including memory storage devices.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above constructions and methods without departing from the scope of the invention, it is intended that all matter contained in the above description and shown in the accompanying drawings shall be interpreted as illustrative and not in a limiting sense.

What is claimed is:

1. A method of performing a certification on an enteral feeding pump based on at least one operating parameter of the pump, the method comprising:
   communicating certification information between the pump and a certification application remote from the pump; and
   verifying that the at least one operating parameter is within a specified operating metric, the at least one operating parameter selected from a group including status of an ultrasonic sensor, status of a power button, status of a rotor encoder, position of a rotor encoder, status of an accelerometer, motor current and ultrasonic sensor voltage;
   wherein communicating certification information comprises receiving at the pump the specified operating metric from the certification application, and wherein verifying that the at least one operating parameter is within the specified operating metric comprises comparing using a processor in the pump the at least one operating parameter against the specified operating metric; and
   delivering nutritional liquid to a patient using the enteral feeding pump, wherein comparing the at least one operating parameter of the pump is performed during delivery of the nutritional liquid to the patient.

2. The method of claim 1, wherein communicating certification information comprises wirelessly communicating the certification information.

3. The method of claim 1, wherein communicating the certification information comprises transmitting a verification to the certification application that the compared at least one operating parameter is within the specified operating metric.

4. The method of claim 1, further comprising making a certification determination whether the at least one operating parameter is within the received specified operating metric and storing the certification determination in a memory of the pump.

5. The method of claim 4, further comprising transmitting the certification determination from the pump to the remote certification application.

6. The method of claim 1, wherein verifying that the at least one operating parameter is within a specified operating metric comprises receiving a manual certification instruction to determine the at least one operating parameter, the manual certification instruction comprising at least one certification step performed manually by a person.

7. The method of claim 1, wherein the at least one operating parameter comprises a first operating parameter with a first specified operating metric and a second operating parameter, the first operating parameter and the second operating parameter being different from each other and being selected from the group consisting of a status of an ultrasonic sensor in the pump, a status of a power button in the pump, a status or position of a rotor encoder in the pump, and a status of an accelerometer in the pump, motor current, and ultrasonic sensor voltage with a corresponding second specified operating metric, and wherein verifying that the at least one operating parameter comprises verifying using a processor at the certification application that the first operating parameter is within the first operating metric, and verifying using the processor in the pump that the second operating parameter is within the second operating metric.

8. An enteral feeding pump for use with a nutritional liquid feeding set to deliver nutritional liquid through the feeding set, the enteral feeding pump comprising:
   a housing capable of receiving at least a portion of the feeding set;
   a pumping device supported by the housing and configured to act on the feeding set to produce fluid flow of the nutritional liquid in the feeding set when the at least a portion of the feeding set is received by the housing;
   a processor configured to determine at least one operating parameter of the enteral feeding pump;
   a memory for storing the at least one operating parameter; and
   a transceiver configured for communication of certification information with a certification application remote from the enteral feeding pump, the certification information including at least one of the at least one operating parameter and an operating metric for the at least one operating parameter, the at least one operating parameter being selected from a group including status of an ultrasonic sensor, status of a power button, status of a rotor encoder, position of a rotor encoder, status of an accelerometer, motor current and ultrasonic sensor voltage;

wherein the processor is configured to determine the at least one operating parameter and the memory is configured to store the at least one operating parameter during operation of the enteral feeding pump to supply the nutritional liquid to a patient.

9. The enteral feeding pump of claim 8, wherein the processor is configured to determine plural distinct operating parameters, including the at least one operating parameter, and the memory is configured to store said plural distinct operating parameters.

10. The enteral feeding pump of claim 8, wherein the transceiver is configured for wireless communication with the remote certification application.

11. The enteral feeding pump of claim 8, wherein the transceiver is configured to transmit the at least one operating parameter to the remote certification application.

12. The enteral feeding pump of claim 8, wherein the transceiver is configured to receive a specified operating metric from the remote certification application and the processor is configured to evaluate the at least one operating parameter against the received specified operating metric.

13. The enteral feeding pump of claim 12, wherein the processor is configured to make a certification determination whether the at least one operating parameter is within the received operating metric and to store the certification determination in the memory.

14. The enteral feeding pump of claim 13, wherein the transceiver is configured to transmit the certification determination to the remote certification application.

15. The enteral feeding pump of claim 8, wherein the transceiver is configured to transmit the at least one operating parameter to the remote certification application for evaluation by the remote certification application against a specified operating metric identified by the remote certification application.

16. The enteral feeding pump of claim 8, wherein the processor is configured to send a signal recommending performing certification on each of the at least one operating parameter if the processor evaluates that at least one operating parameter is outside of a specified operating metric.

17. A method of performing a certification on an enteral feeding pump based on at least one operating parameter of the pump, the method comprising:

communicating certification information between the pump and a certification application remote from the pump;

verifying that the at least one operating parameter is within a specified operating metric, the at least one operating parameter being selected from a group including status of an ultrasonic sensor, status of a power button, status of a rotor encoder, position of a rotor encoder, status of an accelerometer, motor current and ultrasonic sensor voltage; and delivering nutritional liquid to a patient using the enteral feeding pump, wherein verifying the at least one operating parameter of the pump is performed during delivery of the nutritional liquid to the patient.

18. The method of claim 17, wherein communicating the certification information comprises receiving the at least one operating parameter at the certification application, and wherein verifying that the at least one operating parameter is within a specified operating metric comprises comparing using a processor at the certification application the received at least one operating parameter to the specified operating metric.

* * * * *